United States Patent [19]

Wood et al.

[11] 4,252,946
[45] Feb. 24, 1981

[54] PYRIDO-[2,3-D]PYRIMIDINE COMPOUNDS

[75] Inventors: Hamish C. S. Wood, Glasgow; Thomas Paterson, Larkhall, both of Scotland

[73] Assignee: Burroughs Wellcome Co., Research Triangle Park, N.C.

[21] Appl. No.: 891,831

[22] Filed: Mar. 30, 1978

Related U.S. Application Data

[60] Division of Ser. No. 335,102, Feb. 23, 1973, Pat. No. 4,113,859, which is a continuation-in-part of Ser. No. 296,948, Oct. 12, 1972, abandoned.

[30] Foreign Application Priority Data

Oct. 12, 1971 [GB] United Kingdom ............... 47490/71

[51] Int. Cl.³ .................. A61K 31/505; C07D 471/04
[52] U.S. Cl. ..................................... 544/279; 424/251; 544/250; 544/256; 544/312
[58] Field of Search ......................................... 544/279

[56] References Cited

U.S. PATENT DOCUMENTS

| | | |
|---|---|---|
| 3,752,816 | 8/1973 | Cooke et al. .......................... 544/279 |
| 3,862,191 | 1/1975 | El-Haj et al. ......................... 544/279 |
| 3,912,736 | 10/1975 | Noda et al. ........................... 544/279 |
| 3,922,275 | 11/1975 | Noda et al. ........................... 544/279 |
| 4,113,859 | 9/1978 | Wood et al. .......................... 544/279 |

FOREIGN PATENT DOCUMENTS 2250103  4/1973  Fed. Rep. of Germany ........... 544/279

OTHER PUBLICATIONS

Paterson, et al., "J. Chem. Soc.", Perkin Trans. I (GB), No. 8, 1972, pp. 1041–1050.

*Primary Examiner*—Donald G. Daus
*Assistant Examiner*—James H. Turnipseed
*Attorney, Agent, or Firm*—Donald Brown

[57] ABSTRACT

8-Substituted pyrido[2,3-d]pyrimidines having activity against microorganisms which utilize de novo synthesis of riboflavin.

8 Claims, No Drawings

PYRIDO-[2,3-D]PYRIMIDINE COMPOUNDS

This application is a divisional of copending application Ser. No. 335,102, filed Feb. 23, 1973, now issued as U.S. Pat. No. 4,113,859, which is in turn a continuation-in-part of copending application Ser. No. 296,948, filed Oct. 12, 1972, now abandoned.

This invention relates to 8-substituted pyrido[2,3-d]pyrimidines, to methods of making the same and to novel intermediates formed during the process.

Pyrido[2,3-d]pyrimidines without the 8-substituent have been disclosed in the literature. For example, United Kingdom patent specification No. 1,129,084 describes a large number of 2,4,7-triamino-pyrido[2,3-d]pyrimidines having antibacterial and diuretic activity.

The 8-substituted pyrido{2,3-d}pyrimidines of the invention are close structural analogues of the pteridine precursor, indicated by formula (1) in the accompanying sheet of drawings, which is involved in the biosynthesis of riboflavin.

According to the present invention there is provided a pyrido[2,3-d]pyrimidine of formula (A):

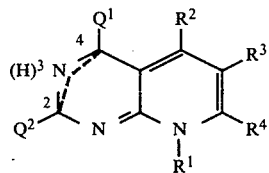

(A)

wherein the dotted line indicates the presence of two additional bonds in the $Q^2$—C(2)—N (3)—C(4)—$Q^1$ moiety, where $Q^1$ and $Q^2$ are the same or different, the N(3) atom carrying a hydrogen atom substituent, and are selected from the class consisting of oxygen and sulphur atoms and the imino group, or one only of $Q^1$ and $Q^2$ is as above defined the other being a halogen atom, a hydroxyl group, an optionally substituted amino, thiol or alkylthio group, $R^2$, $R^3$ and $R^4$ are the same or different and are each a hydrogen atom or an alkyl group containing from 1 to 4 carbon atoms and $R^1$ represents an alkyl or hydroxyalkyl group having from 1 to 6 carbon atoms, or a salt thereof.

When $Q^1$ and $Q^2$ represent oxygen atoms the pyrido[2,3-d]-pyrimidine is normally written in its keto form (B):

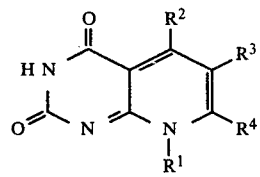

(B)

Such compounds of formula (B) or pharmaceutically acceptable salts thereof are useful as antibacterials, antiprotozoals and antifungals against bacteria, protozoa and fungi which utilize de novo synthesis of riboflavin. An example of bacteria of the above class of microorganisms is E. coli. The preferred compounds of formula B having the antibacterial, antiprotozoal and antifungal activity are those which $R^1$ represents a group of formula —$CH_2$ (CHOH)$_n$ H where n is an integer of from 1 to 5, for example, 1 to 4, especially when $R^1$ represent a D-ribityl group.

When $R^2$, $R^3$ and $R^4$ represent alkyl groups it is preferred that they be methyl groups. In this connection it is interesting to note that the compound 2, 3, 4, 8-tetrahydro-6,7-dimethyl-2,4-dioxo-8-D-ribitylpyrido[2,3-d]pyrimidine has been found to be substantially more active than 2,3,4,8-tetrahydro-5,6-dimethyl-2,4-dioxo-8-D-ribitylpyrido[2,3-d]pyrimidine. The compound 2,3,4,8-tetrahydro-2,4-dioxo-8-D-ribitylpyrido[2,3-d]pyrimidine has also been found to be active.

According to one aspect of the invention there is provided a method of preparing a compound of formula (A) which comprises: (a) reacting a pyrimidine derivative of formula (C) with a compound of formula (D) or sodium salt or acetal or ketal thereof

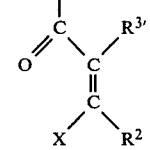

(C)

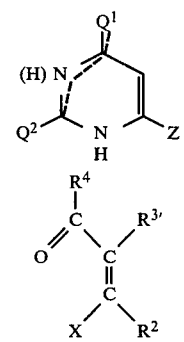

(D)

wherein $Q^1$, $Q^2$, $R^2$ and $R^4$ are as defined above, $R^{3'}$ can be an $R^3$ group, and Z represents the group $NHR^1$, $R^1$ being as defined above, in which case either (i) X is a hydrogen or halogen atom, or an alkoxy, acetyloxy, hydroxy, alkylthio, thiol, or optionally substituted amino group, or (ii) X taken together with $R^{3'}$ represent an additional bond when $R^3$ in the compound of formula (A) represents hydrogen;

(b) when X is hydrogen; removing two superfluous labile hydrogen atoms from the intermediate product formed; and (c) optionally converting said $Q^1$ and/or said $Q^2$ group, when they are substituents other than the oxygen atom or hydroxyl group, into a hydroxyl group or oxygen atom. Replacement of the thiol or alkylthio group or sulphur atom by the hydroxyl group or the oxygen atom can be accomplished by heating with aqueous hydrochloric, hydrobromic or chloroacetic acid, (see for example, page 171 of the book "The Pyrimidines supplement 1" by D. J. Brown, published by Wiley-Interscience in 1970.

The amino group can be converted into the hydroxyl derivative using acid of alkaline hydrolysis or in some cases treatment with nitrous acid. Agents which have been used to accomplish the acid hydrolysis are conc. hydrochloric acid and sulphuric acid (see page 167 et seq of the above book by D. J. Brown).

The halogen atom can be directly converted to a hydroxyl group using acid or alkaline hydrolysis. Acid hydrolysis with refluxing hydrochloric acid can be used but it is preferred that the hydrolysis be carried out in alkaline media, for example, using aqueous sodium hydroxide. As an alternative to the direct hydrolysis of the halogen atom, the halogen atom may be first of all converted into the alkoxy or alkylthio group and this group hydrolysed using acid or alkaline media.

In a preferred embodiment of the invention there is provided a method of preparing a compound of formula (B) which comprises reacting a 4-substituted aminouracil of formula (E)

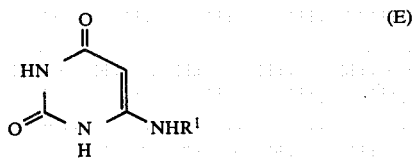

wherein R¹ is as defined above, with a compound of formula (D) where X is a hydrogen atom or a hydroxyl group and, when X is a hydrogen atom, removing two superfluous labile hydrogen atoms from the intermediate product formed.

When X is a hydrogen atom the reaction proceeds via an intermediate which is probably a tricyclic compound (e.g. compound 32 in the charts attached hereto). This intermediate can be converted to the 8-substituted pyrido[2,3-d]pyrimidine by a thermal process, for example, fusing in diphenyl ether or, in some cases, simply by allowing it to stand in an acidic solution for a few days.

When X is a hydroxyl group, the compound of formula (D) can be equally well represented by its aldo or keto form:

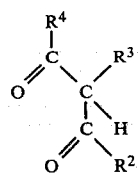

In view of the substantial symmetry of the above compound, and the identity of the interacting functional groups, it is possible that substituents R² and R⁴ will be interchanged in the end product. It has also been suggested that other compounds of formula (D) may react similarly in certain circumstances, to yield a pyridopyrimidine of formula (A) or (B) in which the R² and R⁴ substituents are interchanged. In other words, the X group from the molecule (D) rather than the COR⁴ part of this molecule, may interact with the Z substituent of the molecule of formula (C).

The carbonyl reactants of formula (D) where X is a hydroxyl group are used as such or, preferably, in the form of their sodium salt or their acetal or ketal.

An advantage of the above process when Q¹ and Q² represent oxygen atoms and when Z is the group NHR¹ is that the starting 4-substituted aminouracils are readily available from the reaction of 4-chlorouracil with the appropriate amine. Suitably substituted pyrimidines would be difficult to obtain if one were to consider starting from pyridine precursors.

Compounds of formula (A) where one or both of Q¹ and Q² represent a group other than a hydroxyl group or an atom other than oxygen are useful intermediates in the preparation of compounds of formula B. Accordingly, in a further aspect of the invention, such compounds are provided.

For the treatment of mammalian or avian bacterial, protozoal or fungal infections a compound of formula (B), or a pharmaceutically acceptable salt thereof, may be presented with an acceptable carrier therefor as a pharmaceutical preparation. Suitable pharmaceutically acceptable salts are the sodium and potassium salts. The carrier must of course be 'acceptable' in the sense of being compatible with the other ingredients of the preparation and not deleterious to the recipient of the preparation having regard to the route by which it is intended that the preparation be administered. The carrier may be a solid or liquid, and is preferably formulated with a compound of formula (B) as a unit-dose composition, for example a tablet. The compounds of formula (B) may be incorporated in the preparations either in the form of a base or an acid addition salt thereof, and the preparation formulated by any of the well-known techniques of pharmacy consisting basically of admixture of the components of the preparation.

For oral administration, fine powders or granules of the compounds may contain diluents and dispersing and surface active agents, and may be presented in a draft in water or in a syrup; in capsules or cachets in the dry state or in an aqueous or non-aqueous suspension, when a suspending agent may also be included; in tablets, preferably made from granules of the active ingredient with a diluent, by compression with binders and lubricants; or in a suspension in water or a syrup or an oil or in a water/oil emulsion, when flavouring, preserving, suspending, thickening and emulsifying agents may also be included. The granules or the tablets may be coated, and the tablets may be scored. A suitable tablet may contain from 0.35 to 3.5 grams of active material.

For parenteral administration, the compounds may be presented in unit dose or multi-dose containers in aqueous or non-aqueous injection solutions which may contain antioxidants, buffers, bacteriostats and solutes which render the compounds isotonic with the blood; or in aqueous or non-aqueous suspensions when suspending agents and thickening agents may also be included; extemporaneous injection solutions and suspensions may be made from sterile powders, granules or tablets which may contain diluents, dispersing and surface active agents, binders and lubricants.

For rectal administration the compounds may be presented in association with a base material of low melting point capable of releasing the compound to perform its pharmacological function, which base material when appropriately shaped forms a suppository.

Whilst the routes of administration listed above represent those most likely to be employed, they do not necessarily exhaust the possibilities, which may include topical administration.

The present invention also provides a method of preparinf a pharmaceutical composition which comprises bringing a compound of formula (B) or a pharmaceutically acceptable salt thereof into association with a pharmaceutically acceptable carrier therefor.

Compounds of formula (B) are to be administered to the infected host having bacterial, protozoan or fungal infections at a dosage range of from 3 to 100, preferably from 5 to 50, most preferably from 10 to 30 mg/kg body weight and are to be given three times a day.

Some of the chemistry involved in the present invention is briefly outlined below.

Condensation of 4-(2-hydroxyethylamino) uracil(2) and crotonaldehyde (4) in 20% hydrochloric acid at room temperature gave a single product (8) in good yield (please see attached sheets for key to reference numberals, (N.B. the fact that the carbonyl compound of formula C, where X is hydroxyl group, is shown in its keto form). The product ($C_{10}H_{13}N_3O_3$) was readily converted to 2,3,4,8-tetrahydro-8-(2-hydroxyethyl)-5-methyl-2,4-dioxopyrido[2,3-d]pyrimidine (13) by heating in diphenyl ether. The conversion could also be carried out by holding the intermediate (8) at its melting-point for a short period or by allowing a solution in dilute acid, to stand at room temperature for a few days.

Reaction of the uracil (2) with methylvinyl ketone (5) in 20% hydrochloric acid at room temperature gave an intermediate (9) similar to that mentioned above, and this compound was converted into 2,3,4,8-tetrahydro-8-(2-hydroxyethyl)7-methyl-2,4-dioxopyrido[2,3-d]pyrimidine (14) by refluxing in diphenyl ether. The pyridopyrimidine was different to that obtained from the crotonaldehyde reaction although the n.m.r. spectrum was very similar.

A similar reaction using methacrolein (6) gave the 6-methylpyrido[2,3-d]pyrimidine (15) again via an intermediate compound (10). It seemed likely that the structures of the intermediate compounds (8), (9) and (10) formed in these reactions would be analogous, and this was confirmed by the u.v. spectra which were similar.

The new synthesis of pyrido[2,3-d]pyrimidines was next applied to the synthesis of 8-substituted 5,6-dimethyl pyrido[2,3-d]pyrimidines. Thus, condensation of tiglic aldehyde (7) and the hydroxyethylaminouracil (2) gave us one of the main products a pyridopyrimidine (11) with properties similar to those of the intermediates (8), (9) and (10).

The other major product was the 5,6-dimethyl-pyridopyrimidine (16), which could also be obtained by fusing the intermediate (11) or by heating it in diphenyl ether or boiling water.

4-D-Ribitylaminouracil (3) was treated in a similar fashion with tiglic aldehyde (7) in acid. A product (12) was obtained which could not be crystallised. It did however, exhibit u.v. absorption similar to that of intermediate (11). Treatment in diphenyl ether could not be applied in this case as the product was insoluble in the solvent. Heating the product in 2-ethoxyethanol, or water, for a few hours gave a mixture of products. The 5,6-dimethyl-8-D-ribitylpyridopyrimidine (17) was eventually obtained by holding the crude product at its melting-point for a few minutes. The structure was assigned on the basis of the ultraviolet spectrum which was almost identical to that of the 5,6-dimethyl-8-hydroxyethyl analogue (16), but different from that of the 6,7-dimethyl-8-hydroxyethyl analogue (18), prepared by an alternative method.

Robins and Hitchings *J. Amer. Chem. Soc.*, 1958 80, 3449 have reported that the condensation of 4-aminouracil with β-diketones or β-ketoaldehydes in phosphoric acid at 100° C. yields 1,2,3,4-tetrahydro-2,4-dioxopyrido[2,3-d]pyrimidines. This reaction was applied to the synthesis of 8-substituted pyridopyrimidines from 4-substituted-amino-uracils.

The reaction between 4-(2-hydroxyethylamino) uracil (2) and the sodium salt of 2-methylbutan-3-one-1-al (24) in 85% phosphoric acid gave a low yield of pyrido[2,3-d]pyrimidine. The product differed from the 5,6-dimethyl-pyrido[2,3-d]pyrimidine (16) prepared by using tiglic aldehyde and was formulated as 2, 3, 4, 8-tetrahydro-8-(2-hydroxyethyl)-6,7-dimethyl-2,4-dioxopyrido[2,3-d]pyrimidine (18).

Acetylacetone (25) was condensed in similar fashion with 4-(2-hydroxyethylamino)uracil (2) to give the 5,7-dimethylpyrido[2,3-d]pyrimidine (19). The yields in these reactions were low, however, and it was found that the use of dilute hydrochloric acid in place of 85% phosphoric acid led to increased yields (this is true only for the 4-substituted aminouracils, phosphoric acid remaining the preferred reagent for reactions using 4-aminouracil). A further increase in yield was obtained by using the acetals of the ketoaldehyes rather than the sodium salts.

In this way the acetals (26), (27) and (28) were condensed with the hydroxyethylaminouracil (2) in dilute hydrochloric acid to give the 8-substituted pyrido[2,3-d]pyrimidines (20), (14) and (21) in good yields. The ribitylaminouracil (3) gave analogous products (22) and (23) on condensation with the ketoaldehyde (24) and the acetal (28) respectively.

The pyrido[2,3-d]pyrimidines of formula (A) or the tricyclic intermediates leading thereto may themselves be reduced. Thus, catalytic hydrogenation produces the corresponding reduced compounds such as those of formula (F):

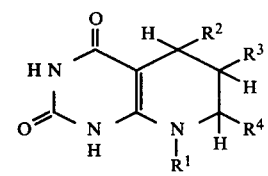

wherein $R^1$, $R^2$, $R^3$ and $R^4$ are as defined above. These compounds of formula (F) have similar antimicrobial activity to the compounds of formula (B).

The invention is illustrated by the following Examples.

EXAMPLES

Ultravoilet spectra were determined using a Unicam-spectrophotometer (Model SP 800 A) on aqueous solutions of standard pH. N.m.r. were determined using either a Perkin-Elmer R10 Spectrometer (60 MHz) or a Varian HA-100 instrument (100 MHz); chemical shifts are expressed in τ units relative to tetramethylsilane (τ10). Infrared spectra were run on a Perkin-Elmer grating spectrophotometer (Model 257) either as liquid films or as pressed discs in KCl. Mass spectra were run on an A.E.I. MS902 Instrument.

Paper chromatograms were developed by the ascending technique using Whatman No. 1 paper with (A) butan-1-ol-5 N-acetic acid (7:3), (B) propan-1-ol-1% aqueous ammonia (2:1), and (C) 3% ammonium chloride as solvents. Spots were located by filtered U.V. light (254 and 365 nm.) and D-ribityl derivatives were further identified using a periodate spray.

Reaction between Crotonaldehyde and 4-(2-Hydroxyethylamino)uracil.

4-(2-Hydroxyethylamino)uracil (5.1 g., 0.03 mole) was dissolved in 20% hydrochloric acid (50 ml.) and freshly distilled crotonaldehyde (5 ml.) was added. On standing overnight at room temperature, colourless crystals precipitated. The product was filtered off. Careful addition of concentrated ammonium hydroxide to the mother-liquour gave a smaller crop of the same product. Recrystallisation from water gave the pyrido[2,3-d]pyrimidine (8) (4.8 g., 72%) as colourless needles, m.p. 249°–252° C. (Found: C,53.8; H,6.19; N,18.48. $C_{10}H_{13}N_3O_3$ requires C,53.81; H,5.83; N,18.83%). High resolution mass measurement of the parent ion in the mass spectrum gave M 223. 09576. $C_{10}H_{13}N_3O_3$ requires M 223.09568.

The product (8) gave no colour when treated with sodium nitrite and acetic acid or sodium nitrate and dilute hydrochloric acid.

2,3,4,8-Tetrahydro-8-(2-hydroxyethyl)-5-methyl-2,4-dioxopyrido[2,3-d]pyrimidine (13).

The product (8) was held at its melting-point for a few minutes to give a new product. The conversion was carried out more satisfactorily by refluxing the product (1 g.) in diphenyl ether (50. ml.) for 2 hr. and precipitating the new product by addition of petroleum ether or hexane. Recrystallisation from aqueous ethanol gave the pyridopyrimidine (0.8 g., 81%) as pale yellow needles, m.p. 295°–298° C. (decomp.) (Found: C,53.62; H,5.11; N,19.05: $C_{10}H_{11}N_3O_3$ requires C,54.30; H,4.98; N,19.00%).

A solution of the product (8) in dilute hydrochloric acid formed the pyridopyrimidine slowly on standing.

1,2,3,4,5,6,7,8-Octahydro-8-(2-hydroxyethyl)-5-methyl-2,4-dioxopyrido [2,3-d]pyrimidine (29)

A solution of the pyridopyrimidine (13) in 5 N-hydrochloric acid was hydrogenated over platinum oxide with uptake of 2 moles of hydrogen per mole of starting material. Work-up in the usual way gave the hydrochloride of (29) as colourless crystals (70%) (Found: C,45.9; H,5.91: N,15.89; Cl,13.7.$C_{10}H_{15}N_3O_3$. HCl requires C,45.9; H,6.12; N,16.09; Cl,13.57%).

The same octahydro-2,4-dioxopyrimidine was obtained by catalytic reduction (uptake 1 mol. of hydrogen) of the intermediate (8).

Reaction between Methyl Vinyl Ketone and 4-(2-Hydroxyethylamino)uracil.

4-(2-Hydroxyethylamino)-uracil (0.34 g., 0.002 mole) and methyl vinyl ketone (0.5 mole) in 20% hydrochloric acid (3.5 ml.) were allowed to stand at room temperature overnight. Careful addition of concentrated ammonium hydroxide precipitated a white powder which on recrystallisation from water gave the pyridopyrimidine (9) (0.14 g., 31%) as clourless crystals, m.p. 266°–267° C. (Found: C,53.68; H,5.91; N,18.75. $C_{10}H_{13}N_3O_3$ requires C,53.81; H,5.83; N,18.83%).

2,3,4,8-Tetrahydro-8-(2-hydroxyethyl)-7-methyl-2,4-dioxopyrido[2,3-d]pyrimidine (14)

(a) 4-(2-Hydroxyethylamino)-uracil (3.4 g., 0.02 mole) was dissolved in the minimum amount of hot O.1 N-hydrochloric acid, and acetoacetaldehyde dimethylacetal (4 ml.) was added. The mixture was refluxed for 2 hrs., cooled and concentrated in vacuo until crystallisation commenced.

The crystals were filtered, washed with hot benzene (to remove any 1,3,5-triacetylbenzene which had formed), and recrystallised from aqueous ethanol to give the pyrido[2,3-d]pyrimidine (2.9 g. 67%) as pale yellow needles, m.p. 314°–316° C. (decomp.) (Found: C,54.70; H,4.98; N,19.08. $C_{10}H_{11}N_3O_3$ requires C,54.30; H,4.98; N,19.00%).

(b) The intermediate pyridopyrimidine (9) was heated in diphenyl ether as for the 5-methyl isomer described above. Recrystallisation of the resultant product from aqueous ethanol gave 2,3,4,8-tetrahydro-8-(2-hydroxyethyl)-7-methyl-2,4-dioxopyrido[2,3-d]pyrimidine (65%), identical with the material prepared in (a) above.

1,2,3,4,5,6,7,8-Octahydro-8-(2-hydroxyethyl)-7-methyl-2,4-dioxopyrido[2,3-d]pyrimidine hydrochloride (30)

2,3,4,8-Tetrahydro-8-(2-hydroxyethyl)-7-methyl-2,4-dioxopyrido [2,3-d]pyrimidine (0.74 g., 0.0033 mole) was dissolved in 5 N-hydrochloric acid (25 ml.) and hydrogenated over platinum oxide (80 mg.). The theoretical 2 equivalents of hydrogen were taken up, and the solution was filtered and concentrated in vacuo until crystallisation occurred. Recrystallisation from ethanol-acetone gave the octahydropyridopyrimidine hydrochloride (0.505 g. 58%) as a white powder, m.p. 204°–206° C. (Found: C,46.01; H,5.66; N,15.29; Cl,13.65. $C_{10}H_{15}N_3O_3$. HCl requires C,45.90; H,6.12; N,16.09; Cl,13.57%).

The same material was obtained by hydrogenation of the intermediate pyridopyrimidine (9) (Uptake 1 mol. hydrogen).

Reaction between Methacrolein and 4-(1-Hydroxyethylamino)uracil

The procedure was repeated as above replacing methyl vinyl ketone with methacrolein. This gave, after recrystallisation from water, the pyridopyrimidine (10) (34%) as colourless crystals, m.p. 250°–252° C. (Found: C,53.62; H,6.35; N,18.54. $C_{10}H_{13}N_3O_3$ requires C,53.81; H,5.83; N,18.83%).

Treatment in diphenyl ether and work-up as before gave 2,3,4,8-tetrahydro-8-(2-hydroxyethyl)-6-methyl-2,4-dioxopyrido (2,3-d)pyrimidine (15), (60%), as pale yellow needles, m.p. 311°–314° C. (decomp.) (Found: C,54.29; H,5.47; N,18.95. $C_{10}H_{11}N_3O_3$ requires C,54.30; H,4.98; N,19.00%).

Reaction of Tiglic Aldehyde and 4-(2-Hydroxyethylamino)uracil

The reaction was carried out in the usual way but was difficult to control. After 24 hr. at room temperature, the reaction mixture contained a considerable amount of fluorescent material as well as three u.v. absorbing products. Careful addition of concentrated ammonium hydroxide solution gave a white precipitate containing one u.v. absorbing product (11) (21%). Recrystallisation from water gave a poor recovery of this product which had been converted to a blue-fluorescent product in about 80% yield. The intermediate (11) was eventually obtained as colourless crystals, m.p. 246°–248° C. (Found; C,55.2; H,6.43; N,17.64. $C_{11}H_{15}N_3O_3$ requires C,55.71; H,6.35; N,17.72%).

The intermediate (11) was converted to 2,3,4β-tetrahydro-8-(2-hydroxyethylamino)-5,6-dimethyl-2,4-dioxopyrido [2,3-d] pyrimidine (16), (78%) in the usual way. Recrystallisation from ethanol gave colourless needles, m.p. 317°–319° C. (decomp.) (Found: C,56.09; H,5.51; N,17.64. $C_{11}H_{13}N_3O_3$ requires C,56.16; H,5.53; N,17.86%). This product was identical in every respect to that obtained during the attempted recrystallisation of product (11) from water.

The mother-liquor of the initial reaction mixture was concentrated in vacuo until crystallisation occurred, giving a product (5%), recrystallisation of which from water gave colourless needles, m.p. 243°–245° C. (decomp.). (Found: C,53.64; H,5.89; N,19.00%).

The mother-liquor was then evaporated to dryness in vacuo, and the residue on recrystallisation from aqueous ethanol gave the pyrido[2,3-d]pyrimidine (16), (27%).

The mother-liquor of the recrystallisation yielded yet another product (2%) as colourless crystals m.p. 215°–216° C. (Found: C,50.00; H,7.79; N,19.28%).

The u.v. spectra of the two minor products were similar to that of the intermediate pyridopyrimidine (11) but we were unable to assign a structure to either of these compounds.

Reaction of 4-D-Ribitylaminouracil and Tiglic Aldehyde.

Tiglic aldehyde (0.4 ml.) was added to a solution of 4-D-ribitylaminouracil (0.4 g., 1.53 mmole in 20% hydrochloric acid and the mixture was left overnight at room temperature.

The mother-liquor was evaporated to dryness in vacuo to give a gum. The product was obtained as an amorphous solid (0.21 g.) by dissolving it in hot ethanol and precipitating by addition of ether. The product became 'tacky' on standing and could not be crystallised, although it appeared to be homogeneous on paper chromatography in systems A,B, and C.

The crude material was refluxed in diphenyl ether but proved to be insoluble and extensive charring occurred.

Heating in 2-ethoxyethanol on a steam bath for 2 hr. resulted in complete conversion of the product to two blue-fluorescent products and several trace products. The faster running of the two blue-fluorescent products was obtained by holding the crude product at its melting-point for a short period. The melt was crushed up in ether and filtered. Attempted purification by dissolving in aqueous ethanol and precipitating with ether, gave a gum, which slowly solidified, on standing for several days, to give 2,3,4,8-tetrahydro-5,6-dimethyl-2,4-dioxo-8-D-ribitylpyrido[2,3-d]pyrimidine (17) as a tan solid, m.p. 246°–247° C. High resolution mass measurement of the parent ion in the mass spectrum gave M 325.12707 $C_{14}H_{19}N_3O_6$ requires M 325.12737.

2,3,4,8-Tetrahydro-8-(2-hydroxyethyl)-6,7-dimethyl-2,4-dioxopyrido[2,3-d]pyrimidine (18).

(a) 4-(2-hydroxyethylamino) uracil (8.5 g., 0.05 mole) was dissolved with gentle heating in 85% phosphoric acid (60 ml.).

The sodium salt of 2-methylbutan-3-one-1-al (85% pure; 6.1. g., 0.05 mole) was added and the mixture was heated for 3 hr. on a steam-bath. The brown mixture was poured into water (250 ml.) and left overnight at 0° C. The precipitate was discarded and the mother-liquor was adjusted to pH 5 with concentrated ammonium hydroxide solution. Refrigeration gave a pale brown precipitate which was recrystallised from water (x4) to give the pyridopyrimidine (1.2 g., 10.0%) as colourless needles, m.p. 310° C. (slow decomposition) (Found: c,56.14; H,5.83; N,17.88. $C_{11}H_{13}N_3O_3$ requires C,56.16; H,5.53; N,17.86%).

(b) 4-(2-Hydroxyethylamino) uracil (3.4 g., 0.02 mole) and the sodium salt of 2-methylbutan-3-one-1-al (85% pure; 2.45 g., 0.02 mole) were refluxed in 0.1 N hydrochloric acid (25 ml.), the mixture being adjusted to pH 2 with 1 N-hydrochloric acid. After 2 hr. the hot solution was filtered and cooled.

Concentration of the solution in vacuo until crystallisation occurred, followed by recrystallisation from aqueous ethanol (charcoal), gave the pyridopyrimidine (2.2 g., 47%) as colourless needles, m.p. 310°–312° C. (decomp.).

(c) The reaction was repeated in 0.1 N-hydrochloric acid but using the dimethylacetal of the ketoaldehyde in place of the sodium salt. Less solvent was required for this procedure and an increase in yield (58%) was obtained.

1,2,3,4,5,6,7,8-Octahydro-8-(2-hydroxyethyl)-6,7-dimethyl-2,4-dioxopyrido[2,3-d]pyrimidine.

2,3,4,8-Tetrahydro-8-(2-hydroxyethyl)-6,7-dimethyl-2,4-dioxopyrido[2,3-d]pyrimidine (0.235 g., 0.001 mole) was suspended in water (25 ml.) and hydrogenated over platinum oxide (100 mg.). After the theoretical uptake of hydrogen (0.002 mole) the catalyst was removed and the filtrate was evaporated to dryness in vacuo. Recrystallisation from aqueous ethanol gave the octahydropyridopyrimidine (0.215 g., 90%) as a white powder, m.p. 244°–247° C. (Found: C,54.8; H,7.10; N,17.70. $C_{11}H_{17}N_3O_3$ requires C,55.24; H,7.11; N,17.98%).

2,3,4,8-Tetrahydro-8-(2-hydroxyethyl)-5,7-dimethyl-2,4 dioxopyrido[2,3-d]pyrimidine (19)

4-(2-Hydroxyethylamino) uracil (3.4 g., 0.02 mole) and acetylacetone (12.0. g., 0.12 mole) were refluxed in 0.1 N-hydrochloric acid (100 ml.) for 7 days. The solution was concentrated in vacuo and refrigerated. The precipitate was filtered and recrystallised from water charcoal to give the pyridopyrimidine (0.65 g., 14.0%) as colourless needles, mp. >360° C.(Found: C,55.86; N,5.68; N,17.7. $C_{11}H_{13}N_3O_3$ requires C,56.16; H,5.53; N,17.86%).

7-Ethyl-2,3,4,8-tetrahydro-8-(2-hydroxyethyl)-2,4-dioxo-pyrido[2,3-d]pyrimidine (20)

4-(2-Hydroxyethylamino) uracil (1.7 g., 0.01 mole) and pentan-3-one-1-al dimethylacetal (1.5 g., 0.01 mole) were refluxed in 0.1 N-hydrochloric acid for 4 hr. and cooled at 0° C. overnight. The precipitate was filtered but contained very little pyridopyrimidine (the solid was probably 1,3,5-tripropionylbenzene). The mother-liquor was reduced in vacuo until precipitation commenced and was then cooled. The product was filtered off and recrystallised from aqueous ethanol to give the pyridopyrimidine (0.76 g., 32.5%) as colourless needles, m.p. 249°–251° C. (decomp.) (Found: C,56.06; H,5.75; N,17.85. $C_{11}H_{13}N_3O_3$ requires c,56.16; H,5.53; N,17.86%).

A further crop of product (0.39 g., 16%) was obtained by concentrating the mother-liquor, cooling, and recrystallising the precipitate from aqueous ethanol.

2,3,4,8-Tetrahydro-8-(2-hydroxyethyl)-2,4-dioxopyrido[2,3-d]pyrimidine (21).

(a) Malondialdehyde tetraethyl-acetal (4.4. g., 0.02 mole) and 4-(2-hydroxyethylamino) uracil (3.42 g. 0.02 mole) were heated in 85% phosphoric acid (25 ml.) for 1 hr. The mixture was poured into water (160 ml) and worked up in the usual way. Recrystallisation from aqueous ethanol (charcoal) gave the pyridopyrimidine (0.46 g., 11%) as pale yellow needles, m.p. 280° C. (decomp.) (Found: C,51.78; H,4.51; N,20.23. $C_9H_9N_3O_3$ requires C,52.17; H,4.35; N,20.29%).

(b) The reaction was repeated in refluxing 0.1 N-hydrochloric acid (25 ml.) for 1 hr. The solution was concentrated in vacuo and cooled. The product was recrystallised from aqueous ethanol to give the pyridopyrimidine (2.73 g., 66%).

2,3,4,8-Tetrahydro-6,7-dimethyl-2,4-dioxo-8-D-ribitylpyrido[2,3-d]pyrimidine (22).

4-D-Ribitylaminouracil (2.6 g., 0.01 mole) and the sodium salt of 2-methylbutan-3-one-1-al (85% pure; 1.22 g., 0.01 mole) were refluxed in 0.5 N-hydrochloric acid (40 ml.) for 2 hrs. The solution was filtered and concentrated in vacuo to about 5 ml. Ethanol was added until precipitation began and the mixture was refrigerated. The product was collected and recrystallised from aqueous ethanol to give the pyridopyrimidine (0.65 g. 20%) as colourless needles, mp. 247°–249° C.) (decomp.) (Found: C,51.52; H,6.66; N,11.53. $C_{14}H_{19}C_3O_6.CH_3CH_2OH$ requires C,51.75; H,6.74; N,11.32%).

The mother liquour of the reaction was again concentrated in vacuo and treated with ethanol as above. The precipitate contained several impurities and recrystallisation from aqueous ethanol gave a gel which slowly formed crystals on standing. Repeated recrystallisation gave a further crop of the pure product (0.41 g., 12.6%) as colourless needles.

2,3,4,8-Tetrahydro-2,4-dioxo-8-D-ribitylpyrido[2,3-d]pyrimidine (23).

4-D-Ribitylaminouracil (2.61 g., 0.01 mole) and malondialdehyde tetraethylacetal (2.2 g., 0.01 mole) were refluxed in 0.1 N-hydrochloric acid (10 ml.) for 1 hr. The red solution was treated with decolourising charcoal, filtered and concentrated in vacuo to about 3 ml. Ethanol was added to effect precipitation. The precipitate was recrystallised from aqueous ethanol (charcoal) to give the ribitylpyridopyrimidine (1.22 g., 41%) as off-white crystals, m.p. 228°–230° C. (decomp.) (Found: C, 48.48; H, 5.21; N, 14.12. $C_{12}H_{15}N_3O_6$ requires C, 48.49; H, 5.05; N, 14.14%).

EXAMPLE 2

A tablet was made up from the following ingredients:

| | | |
|---|---|---|
| (i) | 2,3,4,8-tetrahydro-6,7-dimethyl-2,4-dioxo-8-D-ribitylpyrido [2,3-d] pyrimidine | 350mg |
| (ii) | Starch B.P. | 75mg |
| (iii) | Gelatin B.P. | 7mg |
| (iv) | Magnesium stearate | 10mg |

Components (i) and (ii) were mixed together and granulated with a 10% solution of component (iii) in purified water B.P. The aqueous mixture was then dried. The dried material was mixed with the magnesium stearate and compressed into a tablet.

EXAMPLE 3

A suspension was made up from the following ingredients

| | | |
|---|---|---|
| (i) | 2,3,4,8-tetrahydro-2,4-dioxo-8-D-ribitylpyrido [2,3-d] pyrimidine | 125mg |
| (ii) | Compound Tragacanth Powder B.P. | 10mg |
| (iii) | Sucrose | 2.0g |
| (iv) | Glycerin | 0.5g |
| (v) | Oil of aniseed | 0.001ml |
| (vi) | Alchohol B.P. 95% | 0.01ml |
| (vii) | Purified water B.P. | to 5ml |

Component (i) was dispersed in a gel prepared from components (ii), (iii), (iv) and half of (vii). To this dispersion there was added component (v) as a solution in component (vi). The remainder of (vii) was then added to complete the suspension.

EXAMPLE 4

Preparation of 2,3,4,8-Tetrahydro-7-methyl-2, 4-dioxo-8-D-ribitylpyrido[2,3-d]pyrimidine 4-D-Ribitylaminouracil (0.52 g) in 0.5 N hydrochloric acid (10 ml) was added to acetoacetaldehyde-dimethylacetal (1 ml). This mixture was refluxed for 2 hours. The deep red solution (which showed characteristic U.V. absorption at 356 nm and 322 nm at pH 1) was neutralised to pH 7 with dilute sodium hydroxide and evaporated at 40° C. to 2 ml. This solution was chromatographed on a column (20 cm × 3.5 cm) of Amberlite CG-50 cation-exchange resin. The product was eluted with water, the column fractions being assayed by U.V. absorption. Evaporation of the aqueous eluent (700 ml) gave a brown oil which solidified on treatment with ethanol. Recrystallisation from ethanol/water gave pale yellow needles (304 mg) of 2,3,4,8-tetrahydro-7-methyl-2, 4-dioxo-8-D-ribitylpyrido[2,3-d]pyrimidine

| | | |
|---|---|---|
| I.R. | | (KBr disc) |
| | | 3500–3100 cm$^{-1}$ (broad OH) |
| $v_{max}$ | | |
| | | 1695 cm$^{-1}$ (carbonyl) |
| NMR | | (100 MHz in D$_2$O) |
| | γ7.18 | (3H, singlet, CH$_3$—) |
| | 6.40–4.97 | (broad multiplet + H$_2$O peak, ribityl) |
| | 2.86 | (1H, doublet J = 9Hz, 6-H) |
| | 1.54 | (1H, doublet J = 9Hz, 5-H) |
| UV | | |
| | | 356, 323, 276 nm (pH1) |
| $\lambda_{max}$. | | |
| | | 367, 262 nm (pH13) |

EXAMPLE 5

Preparation of 2,3,4,8-Tetrahydro-6-methyl-2, 4-dioxo-8-D-ribitylpyrido[2,3-d]pyrimidine 4-D-Ribitylaminouracil (0.80 g) was dissolved in a mixture of water (8 ml) and concentrated hydrochloric acid (2 ml). The solution was added to methacrolein (1 ml) and the mixture was stirred at room temperature for 30 minutes. After standing overnight, the reaction mixture was evaporated to a gum which was then redissolved in the minimum amount of hot ethanol. On addition of ether (large excess) to the cooled ethanolic solution a white solid was obtained. This rapidly turned gummy on filtration and consequently was dissolved in ethoxyethanol (30 ml). This solution was refluxed for 4 hours while bubbling oxygen through the solution. Ether (200 ml) was added to this solution on cooling, and the resultant tan coloured solid was obtained by filtration. The solid was dissolved in water (2 ml) and chromatographed on a column of Amberlite CG-50 as described above.

Evaporation of the aqueous eluent gave a yellow solid which was recrystallised from ethanol/water to give 2,3,4,8-tetrahydro-6-methyl-2,4-dioxo-8-D-ribitylpyrido[2,3-d]pyrimidine (123 mg).

| | |
|---|---|
| IR | (KBr disc) |
| | 3500–3080 cm$^{-1}$ (broad OH) |
| $v_{max}$ | |
| | 1685 cm$^{-1}$ (carbonyl) |

| | |
|---|---|
| NMR | (100 MHz in D$_2$O) |
| γ7.63 | (3H, singlet, CH$_3$—) |
| 6.33 –4.95 | (broad envelope + H$_2$O peak-ribityl) |
| 1.68 | (1H, doublet, J = 2Hz) |
| 1.56 | (1H, doublet, J = 2Hz) |
| UV | |
| λ$_{max}$ | 356, 325, 275 nm (pH1) |
| | 373, 257.5 nm (pH 13) |

EXAMPLE 6

Preparation of 2,3,4,8-Tetrahydro-5-methyl-2,4-dioxo-8-D-ribityl-pyrido[2,3-d]pyrimidine 4-D-Ribitylaminouracil (0.80 g) was dissolved in a mixture of water (8 ml) and concentrated hydrochloric acid (2 ml). The solution was added to crotonaldehyde (1 ml) and the mixture was stirred at room temperature for 2 hours. After standing overnight the reaction mixture was evaporated at 40° C. to a gum which was then redissolved in the minimum of hot ethanol. Addition of ether to the cooled ethanolic solution gave a white solid which became sticky on filtration. The solid was dissolved in ethoxyethanol (30 ml) and this was refluxed for 2 hours while bubbling oxygen through the solution. The solution turned very dark. Addition of ether (200 ml) to the cooled solution gave a brown precipitate. This was filtered off, redissolved in water (2 ml) and chromatographed on a column of Amberlite CG-50 as described above.

Evaporation of the aqueous eluent gave a cream solid, which was crystallised from ethanol/water to give the 2,3,4,8-tetrahydro-5-methyl-2,4-dioxo-8-D-ribitylpyrido[2,3-d]pyrimidine (98 mg).

| | |
|---|---|
| IR | (KBr disc) |
| ν$_{max}$ | 3540–3030 cm$^{-1}$ (broad OH) |
| | 1685 cm$^{-1}$ (carbonyl) |
| NMR | (100 MHz in CF$_3$ COOH) |
| γ 6.88 | (3H singlet, CH$_3$—) |
| 5.93–4.73 | (7H, multiplet, ribityl) |
| 2.41 | (1H, doublet, J = 8Hz, 6-H) |
| 1.37 | (1H, doublet, J = 8Hz, 7-H) |
| UV | |
| λ$_{max}$ | 346, 311, 275 nm (pH 1) |
| | 357, 256 nm (pH 13) |

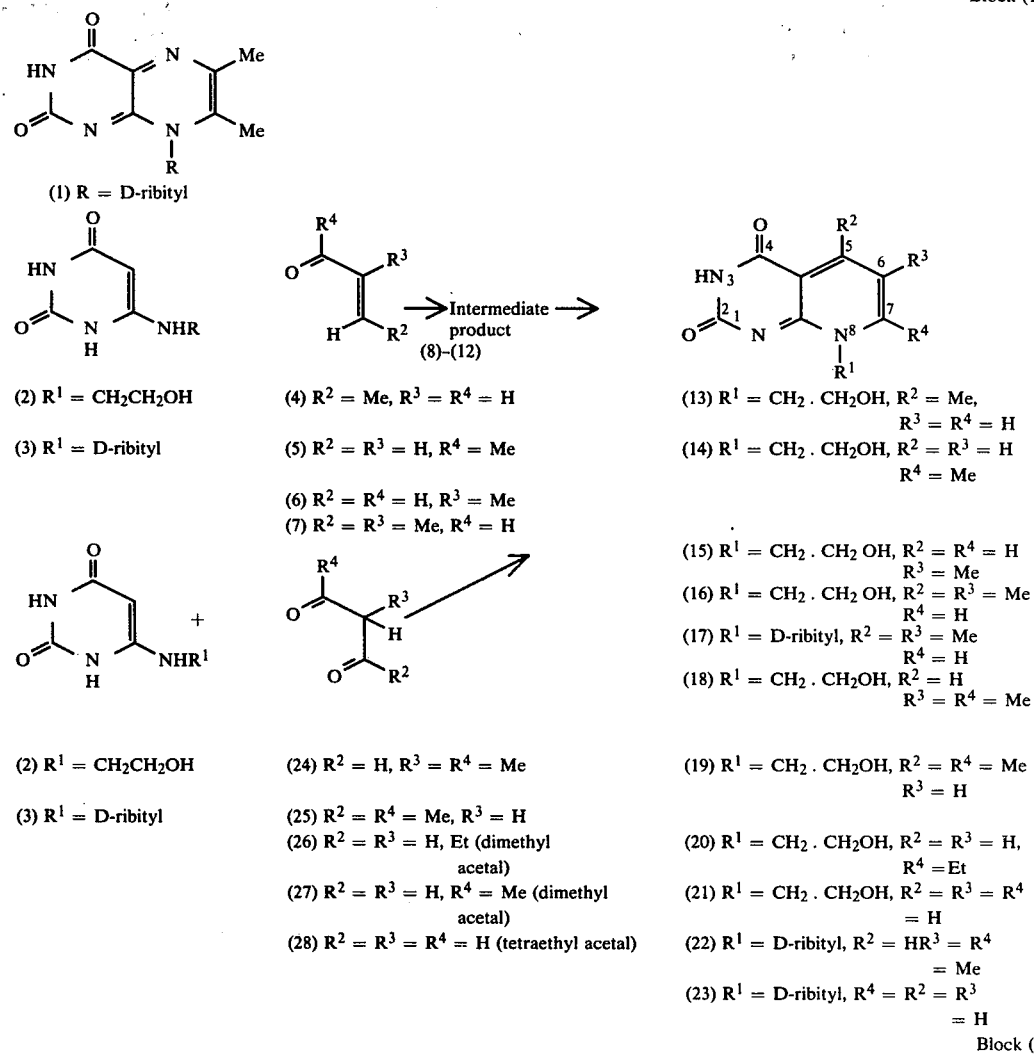

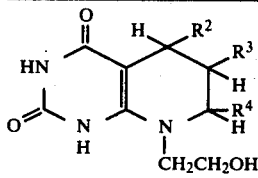

(29) R² = Me, R³ = R⁴ = H
(30) R² = R³ = H, R⁴ = Me
(31) R² = R⁴ = H, R³ = Me

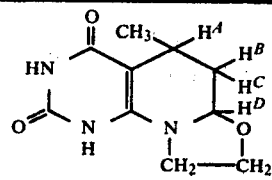

(32)

What is claimed is:

1. A pyrido[2,3-d]pyrimidine of formula (B)

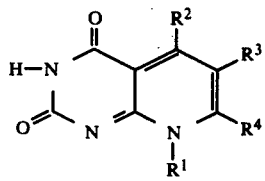

(B)

wherein $R^1$ is alkyl of 1 to 6 carbon atoms or hydroxyalky of 1 to 6 carbon atoms or $-CH_2(CHOH)_n H$ where n is 1 to 5 and wherein $R^2$, $R^3$ and $R^4$ are the same or different and can each represent hydrogen or alkyl having from 1 to 4 carbon atoms.

2. A pyrido[2,3-d]pyrimidine according to claim 1 in which $R^1$ represents a D-ribityl group.

3. A pyrido[2,3-d]pyrimidine of formula (B) as defined in claim 1 wherein $R^1$ represents a D-ribityl group.

4. 2,3,4,8-Tetrahydro-5,6-dimethyl-2,4-dioxo-8-D-ribitylpyrido[2,3-d]pyrimidine.

5. 2,3,4,8-Tetrahydro-2,4-dioxo-8-D-ribitylpyrido[2,3-d]pyrimidine.

6. 2,3,4,8-Tetrahydro-6,7-dimethyl-2,4-dioxo-8-D-ribitylpyrido[2,3-d]pyrimidine.

7. A pyrido[2,3-d]pyrimidine according to claim 1 wherein one of $R^2$, $R^3$ and $R^4$ is methyl.

8. A pyrido[2,3-d]pyrimidine according to claim 1 wherein $R^2$, $R^3$ and $R^4$ are each methyl.

* * * * *